(12) United States Patent
Li et al.

(10) Patent No.: US 7,989,532 B2
(45) Date of Patent: Aug. 2, 2011

(54) RGD POLYPEPTIDE GRAFTED POLY (GLYCOLIC ACID-L-LYSINE-L-LACTIC ACID) / β TRICALCIUM PHOSPHATE COMPOSITE MATERIAL AND PREPARATION METHOD THEREOF

(75) Inventors: Shipu Li, Wuhan (CN); Yingchao Han, Wuhan (CN); Yuhua Yan, Wuhan (CN); Tao Wan, Wuhan (CN); Xinyu Wang, Wuhan (CN); Lin Yuan, Wuhan (CN); Honglian Dai, Wuhan (CN); Qiongjiao Yan, Wuhan (CN)

(73) Assignee: Wuhan University of Technology, Wuhan (CN)

( * ) Notice: Subject to any disclaimer, the term of this patent is extended or adjusted under 35 U.S.C. 154(b) by 0 days.

(21) Appl. No.: 12/170,643

(22) Filed: Jul. 10, 2008

(65) Prior Publication Data

US 2008/0319114 A1 Dec. 25, 2008

Related U.S. Application Data

(63) Continuation of application No. PCT/CN2006/001863, filed on Jul. 26, 2006.

(30) Foreign Application Priority Data

Jun. 29, 2006 (CN) .......................... 2006 1 0019493

(51) Int. Cl.
*C08K 3/32* (2006.01)
*C08K 3/10* (2006.01)
*C08K 3/22* (2006.01)
*C07K 1/04* (2006.01)
*C08F 283/00* (2006.01)
*C08G 63/48* (2006.01)
*C08G 63/91* (2006.01)

(52) U.S. Cl. ...................... 524/417; 524/436; 525/54.11

(58) Field of Classification Search ................ 524/417, 524/436; 525/54.11
See application file for complete search history.

(56) References Cited

U.S. PATENT DOCUMENTS

| 5,399,665 | A | * | 3/1995 | Barrera et al. | 528/354 |
|---|---|---|---|---|---|
| 5,955,529 | A | * | 9/1999 | Imai et al. | 524/417 |
| 5,977,204 | A | * | 11/1999 | Boyan et al. | 523/113 |
| 6,165,486 | A | * | 12/2000 | Marra et al. | 424/423 |
| 6,344,496 | B1 | * | 2/2002 | Niederauer et al. | 523/113 |
| 6,441,073 | B1 | * | 8/2002 | Tanaka et al. | 524/414 |
| 6,541,022 | B1 | * | 4/2003 | Murphy et al. | 424/422 |
| 7,056,968 | B2 | * | 6/2006 | Hiraide et al. | 524/414 |
| 7,150,879 | B1 | * | 12/2006 | Lee et al. | 424/422 |
| 7,427,394 | B2 | * | 9/2008 | Anderson et al. | 424/78.37 |
| 2002/0022883 | A1 | * | 2/2002 | Burg | 623/8 |
| 2002/0082220 | A1 | * | 6/2002 | Hoemann et al. | 514/21 |
| 2002/0127391 | A1 | * | 9/2002 | Kumar | 428/325 |
| 2004/0086479 | A1 | * | 5/2004 | Grinstaff et al. | 424/78.17 |
| 2005/0079470 | A1 | * | 4/2005 | Rutherford et al. | 433/226 |
| 2005/0161857 | A1 | * | 7/2005 | Coombes et al. | 264/172.15 |
| 2006/0067909 | A1 | * | 3/2006 | West et al. | 424/78.27 |
| 2007/0042341 | A1 | * | 2/2007 | Xu et al. | 435/2 |
| 2007/0077270 | A1 | * | 4/2007 | Wen | 424/423 |
| 2008/0319114 | A1 | * | 12/2008 | Li et al. | 524/415 |
| 2009/0148489 | A1 | * | 6/2009 | Cooper | 424/423 |

OTHER PUBLICATIONS

Kim et al., Tissue Engineering, 12(2), 2006, 221-233.*
Barrera et al. J. Am Chem. Soc, 115, 1993, 11010-11011.*
Cook et al., Journal of Biomedical Materials Research, 35, 513-523, 1997.*
Yoon et al., Biomaterials 25, 2004, 5613-5620.*

* cited by examiner

*Primary Examiner* — Mark Eashoo
*Assistant Examiner* — Liam Heincer
(74) *Attorney, Agent, or Firm* — Matthias Scholl P.C.; Matthias Scholl

(57) ABSTRACT

An RGD polypeptide grafted poly (glycolic acid-L-lysine-L-lactic acid)/β-tricalcium phosphate composite material is composed of β-tricalcium phosphate particles and RGD polypeptide grafted poly (glycolic acid-L-lysine-L-lactic acid) with mass ratio of 1:10-1:100, in which the β-tricalcium phosphate particles are uniformly dispersed in the RGD polypeptide grafted poly (glycolic acid-L-lysine-L-lactic acid) matrix. The preparation method includes that poly (glycolic acid-L-lysine-L-lactic acid) is polymerized with GRGDY short peptide (glycin-arginine-glycin-aspartic acid-tyrosine sequence) to obtain RGD polypeptide grafted poly (glycolic acid-L-lysine-L-lactic acid), and then RGD polypeptide grafted poly (glycolic acid-L-lysine-L-lactic acid) is compounded with β-tricalcium phosphate particles. The composite material exhibits favorable biocompatibility, cellular affinity, biodegradability and mechanical behavior, and can avoid aseptic necrosis of tissues, which may be used as nerve guide or porous bone scaffold for repairing nerve tissue and bone tissue.

15 Claims, 1 Drawing Sheet

RGD POLYPEPTIDE GRAFTED POLY (GLYCOLIC ACID-L-LYSINE-L-LACTIC ACID) / β TRICALCIUM PHOSPHATE COMPOSITE MATERIAL AND PREPARATION METHOD THEREOF

CROSS-REFERENCE TO RELATED APPLICATIONS

This application is a continuation of International Patent Application No. PCT/CN2006/001863 with an international filing date of Jul. 26, 2006, designating the United States, now pending, and further claims priority benefits to Chinese Patent Application No. 200610019493.9, filed on Jun. 29, 2006. The contents of these specifications are incorporated herein by reference.

BACKGROUND OF THE INVENTION

1. Field of the Invention

This invention relates to a biomaterial in the field of tissue engineering for repairing nerve tissue and bone tissue. Specifically, the present invention relates to an RGD polypeptide grafted poly (glycolic acid-L-lysine-L-lactic acid)/β-tricalcium phosphate composite material, which is used to prepare nerve conduit or porous bone scaffold so as to repair the defects of nerve tissue or bone tissue. A method for preparing the composite material is also described.

2. Description of the Related Art

Tissue defects such as peripheral nerve defects are clinical common injuries. Natural bioactive materials, such as autologous nerve, skeletal muscle, blood vessel, membranous tubule, are mainly used in the traditional ways for repairing the peripheral nerve defects. However, these methods exhibit some shortcomings, for example, the second surgery, limited quantity of autologous bioactive materials. In addition, the collapse, due to short of blood, would cause hypoplasty and adhesion of tissue, which could further lead to scar tissue hyperplasia. Moreover, nerve allograft transplantation can also be used, but exhibits the problems of immune response and low success rate. In addition, the non-natural biomaterials such as demineralized bone tube, nylon fibre tube, silica gel pipe, polyurethane tube can also be utilized to repair the nerve tissue defect. Nevertheless, they can not be degraded and absorbed by human body and need to be taken out by the second surgery resulting in the damage of nerve tissue again.

In order to solve the problems described above, researchers are always making great efforts to look for the biodegradable materials which can repair the tissue defects. Now the biomaterials for preparing nerve conduit are mainly some biodegradable natural polymers and synthetic polymers. The natural polymers such as collagen and fibrin possess cell identification signal due to the specific amino acid sequence, which is advantageous to cell adhesion. They have good biocompatibility and cellular affinity. But the disadvantages are the poor degradation property and poor mechanical behavior. The degradation property and mechanical behavior of the synthetic polymers such as poly (glycolic acid) (PGA), poly (lactic acid) (PLA) and poly (lactic-co-glycolic acid) (PLGA) are better than the natural polymers. However, the biocompatibility and cellular affinity of synthetic polymers are worse than natural polymers. Moreover, the catabolite of synthetic polymers exhibits acidity, which will easily result in the aseptic necrosis of tissue.

SUMMARY OF THE INVENTION

The objective of this invention is to provide an RGD polypeptide grafted poly (glycolic acid-L-lysine-L-lactic acid)/β-tricalcium phosphate composite material, exhibiting good biocompatibility, good cellular affinity, good degradation property and good mechanical behavior, as well as effective avoidance of aseptic necrosis, and the preparation method.

In order to realize the objectives mentioned above, the proposed RGD polypeptide grafted poly (glycolic acid-L-lysine-L-lactic acid)/β-tricalcium phosphate composite material of the invention is formed by combination of β-tricalcium phosphate particles and RGD polypeptide grafted poly (glycolic acid-L-lysine-L-lactic acid).

The molecular weight of RGD polypeptide grafted poly (glycolic acid-L-lysine-L-lactic acid) is 30,000-300,000 and the mole content of L-lysine in RGD polypeptide grafted poly (glycolic acid-L-lysine-L-lactic acid) is 0.1%-5%. The molecular structure of RGD polypeptide grafted poly (glycolic acid-L-lysine-L-lactic acid) is shown as follows, wherein X: Y=1:10-1:500.

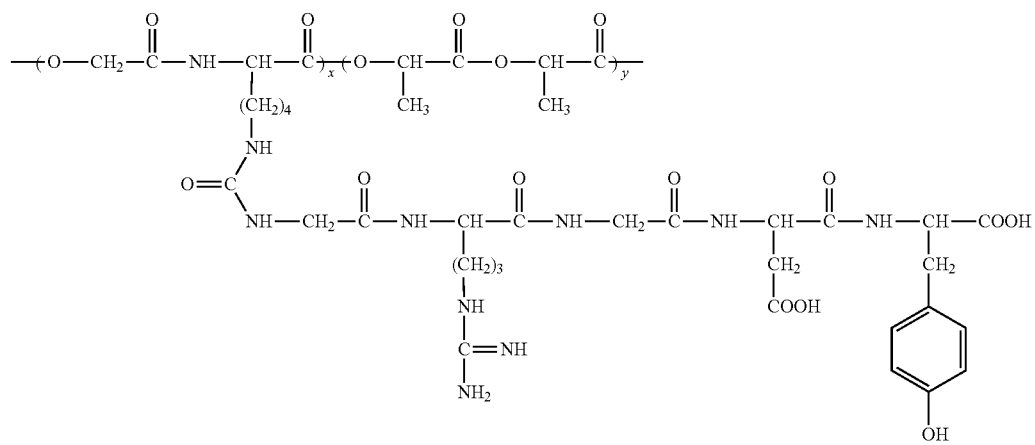

The β-tricalcium phosphate particles are uniformly dispersed in the RGD polypeptide grafted poly (glycolic acid-L-lysine-L-lactic acid) matrix, and the mass ratio of β-tricalcium phosphate particles to RGD polypeptide grafted poly (glycolic acid-L-lysine-L-lactic acid) is between 1:10 and 1:100.

The preparation method of RGD polypeptide grafted poly (glycolic acid-L-lysine-L-lactic acid)/β-tricalcium phosphate composite material includes the following steps:

1) Firstly, poly (glycolic acid-L-lysine-L-lactic acid) is polymerized with GRGDY short peptide (glycin-arginine-glycin-aspartic acid-tyrosine sequence, Gly-Arg-Gly-Asp-Tyr) to obtain RGD polypeptide grafted poly (glycolic acid-L-lysine-L-lactic acid) by grafting RGD (arginine-glycin-aspartic acid sequence, Arg-Gly-Asp) in GRGDY short peptide on the side amino groups of L-lysine in poly (glycolic acid-L-lysine-L-lactic acid);

2) Then, the generated RGD polypeptide grafted poly (glycolic acid-L-lysine-L-lactic acid) is dissolved in organic solvent, and β-tricalcium phosphate particles are added into the organic solution of RGD polypeptide grafted poly (glycolic acid-L-lysine-L-lactic acid). The mixture is uniformly mixed;

3) Subsequently, the RGD polypeptide grafted poly (glycolic acid-L-lysine-L-lactic acid)/β-tricalcium phosphate composite material is obtained with the volatilization of the organic solvent mentioned above by vacuum drying.

The poly (glycolic acid-L-lysine-L-lactic acid) mentioned above is prepared by the polymerization of L-Lys and α-hydroxy acid (glycolic acid, L-lactic acid). Specifically, $N^\epsilon$-benzyloxycarbonyl-L-lysine reacts with bromoacetyl bromide to obtain 3-[4-(benzyloxycarbonylamino) butyl]-morpholine-2,5-dione monomer, which is polymerized with L-lactide to obtain poly (glycolic acid-$N^\epsilon$-benzyloxycarbonyl-L-lysine-L-lactic acid). Finally, the resultant polymer undergoes the catalytic hydrogenolysis by Pd/C to eliminate benzyloxycarbonyl group and the poly (benzyloxycarbonyl-L-Lysine-L-lactic acid) is obtained.

The invention utilizes the intrinsic advantages of natural polymers and synthetic polymers, which are compounded together and grafted with RGD polypeptide. Then the poly (glycolic acid-L-lysine-L-lactic acid), grafted with RGD polypeptide, and β-tricalcium phosphate powder particle are compounded. The compounded β-tricalcium phosphate (1-TCP) is one kind of biodegradable ceramic materials with good biocompatibility, which can be used to repair bone tissue defects. When the β-TCP particles are compounded to polymer biodegradable materials, β-TCP can improve the mechanical strength of nerve conduit and release calcium ions ($Ca^{2+}$) and phosphate ions ($PO_4^{3-}$) while degradation. Moreover, its catabolite exhibits low basicity, which can neutralize the acidity derived from the degradation of polymer, and the calcium is also the important element to improve the growth of neuron. The Arg-Gly-Asp (RGD) sequence contained in grafted polypeptides can identify cells, combining receptors on cell surface, and lead cell adhesion, enhancing cell adhesive force. Therefore, the composite material of this invention exhibits not only good biocompatibility and good cellular affinity as natural polymers but also good degradation property and good mechanical behavior as synthetic polymers. Meanwhile, the composite material can adjust the acid environment due to the degradation of polymer and avoid the aseptic necrosis of tissue. The composite material is very suitable to be used as nerve guide or porous bone scaffold for repairing nerve tissue and bone tissue.

DETAILED DESCRIPTION OF THE INVENTION

Figure 1:
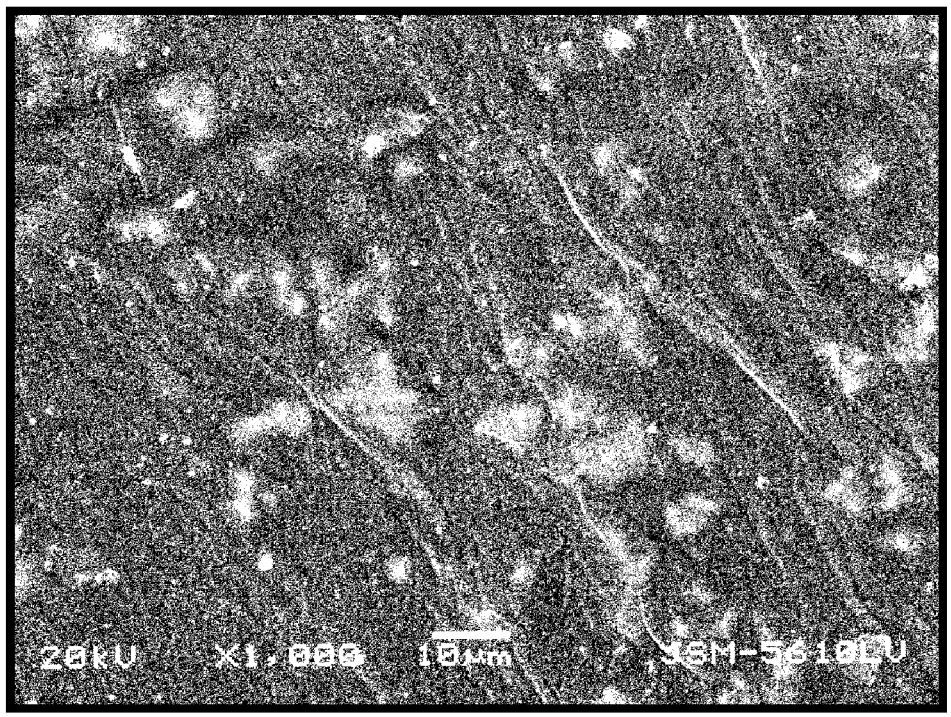
FIG. 1 is a schematic diagram of Microstructure of RGD polypeptide grafted poly (glycolic acid-L-lysine-L-lactic acid)/β-tricalcium phosphate composite material under the microscope (×1000)

The RGD polypeptide grafted poly (glycolic acid-L-lysine-L-lactic acid)/β-tricalcium phosphate composite material and the preparation method will be further described in detail.

Embodiment 1

The preparation method of RGD polypeptide grafted poly (glycolic acid-L-lysine-L-lactic acid)/β-tricalcium phosphate composite material includes the following steps:

1) Preparing 3-[4-(Benzyloxycarbonylamino) Butyl]-Morpholine-2,5-Dione Monomer 50 ml triethylamine $(C_2H_5)_3N$ and 50 g $N^\epsilon$-benzyloxycarbonyl-L-lysine acid are added to 500 ml 1,4-dioxane $(C_4H_8O_2)$. Then 30 ml bromoacetyl bromide ($BrCH_2COBr$) is dropped into the above-mentioned 1,4-dioxane solution at 10-25° C. The reaction is followed by Thin Layer Chromatography (TLC). The reaction product is extracted by diethyl ether twice. The extract is washed by water twice or three times, dried by sodium sulfate. The solvent is recovered in vacuum, and the residual products are used for next reaction.

The residual products are dropped to 1500 ml N,N'-Dimethylformamide (DMF) suspension liquid containing 39 g $NaHCO_3$ at 50-110° C. The reaction is followed by TLC. After reclaiming of the solvent in vacuum, the reaction product is extracted by ethyl acetate several times, washed by water twice or three times and dried by sodium sulfate. After reclaiming of the solvent in vacuum, waxy solid is obtained. Then the waxy solid is dissolved in acetic ether and purified by column chromatography. Subsequently, the obtained acetic ether is evaporated in vacuum to obtain the coarse product of 3-[4-(benzyloxycarbonylamino) butyl]-morpholine-2,5-dione monomer, which is finally recrystallized by acetic ether/n-hexane to obtain 3-[4-(benzyloxycarbonylamino) butyl]-morpholine-2,5-dione monomer.

2) Preparing Poly (Glycolic Acid-$N^\epsilon$-Benzyloxycarbonyl-L-Lysine-L-Lactic Acid)

According to the molar ratio of L-Lactide/3-[4-(benzyloxycarbonylamino) butyl]-morpholine-2,5-dione monomer-= 1: 9, 40.5 g L-Lactide and 10 g 3-[4-(benzyloxycarbonylamino) butyl]-morpholine-2,5-dione monomer are weighed and put into ampule. Then 5 ml stannous octoate chloroform solution of 30 mg/ml is injected. After volatilization of the chloroform under vacuum, the ampule is sealed with alcohol blast burner. Finally, the sealed ampule is put into oil-bath of 90-140° C. for 12-72 h to obtain poly (glycolic acid-$N^\epsilon$-benzyloxycarbonyl-L-lysine-L-lactic acid).

3) Preparing Poly (Glycolic Acid-L-Lysine-L-Lactic Acid)

20 g poly (glycolic acid-$N^\epsilon$-benzyloxycarbonyl-L-lysine-L-lactic acid) is dissolved in 200 ml chloroform and undergoes the catalytic hydrogenolysis by 1 g 10% Pd/C to eliminate benzyloxycarbonyl group, which results in poly (glycolic acid-L-lysine-L-lactic acid).

4) Preparing RGD Polypeptide Grafted Poly (Glycolic Acid-L-Lysine-L-Lactic Acid)

First, dissolve 10 g poly (glycolic acid-L-lysine-L-lactic acid) in 300 ml methylene chloride ($CH_2Cl_2$) and add 450 ml dimethyl sulfoxide (DMSO). Then 0.5-1.6 g GRGDY short peptide (Gly-Arg-Gly-Asp-Tyr) and 0.5 g N,N'-Carbonyldi-imidazole (CDI) are added to the above-mentioned solution. The mixture is kept for 3-5 h at 0-5° C. and then $CH_2Cl_2$ is reclaimed in vacuum. After residual liquid becoming opacity, water is added and polymer is separated out. The polymer is filtered and dried in high vacuum to obtain the RGD polypeptide grafted poly (glycolic acid-L-lysine-L-lactic acid) with molecular weight of 30,000-150,000. The mole content of L-lysine in RGD polypeptide grafted poly (glycolic acid-L-lysine-L-lactic acid) is 2%-5%. The molecular structure of RGD polypeptide grafted poly (glycolic acid-L-lysine-L-lactic acid) is shown as follows, wherein X:Y=1:10-1:500.

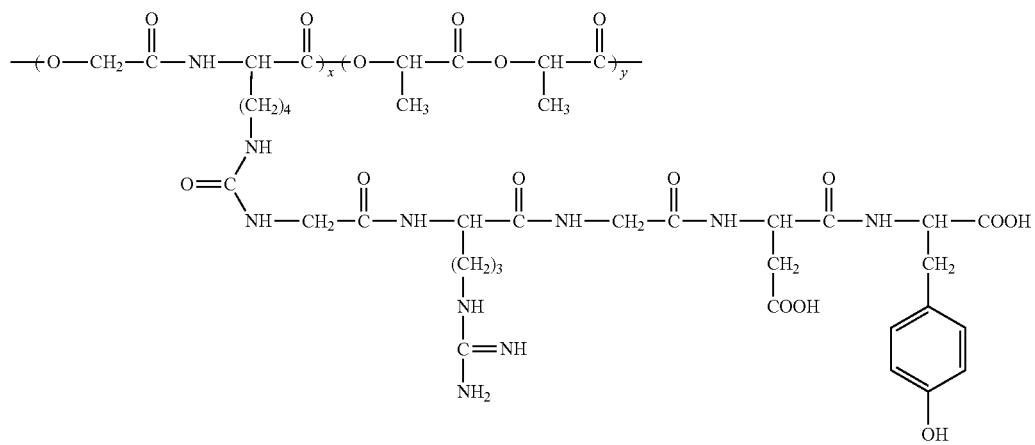

5) Preparing β-TCP Particle

β-TCP particles are synthesized by a solid state method. When 34.4 g $CaHPO_4.2H_2O$ and 10 g $CaCO_3$ are mixed uniformly, the mixture is directly calcined at about 940° C. to obtain powder. Then β-TCP powder is milled in water for 8-12 h by ball milling, and then dried. After that, the dried β-TCP powder is dispersed in absolute alcohol and classified. Then, the β-TCP powder is dried again to obtain β-TCP particles between 0.05 μm and 2 μm in diameter for standby.

6) Preparing an RGD Polypeptide Grafted Poly (Glycolic Acid-L-Lysine-L-Lactic Acid)/β-TCP Particle Composite Material First, 10 g RGD polypeptide grafted poly (glycolic acid-L-lysine-L-lactic acid) is dissolved in chloroform. Then 0.2 g β-TCP particles are added to the above-mentioned solution and dispersed by ultrasonic wave. After volatilization of solvent, RGD polypeptide grafted poly (glycolic acid-L-lysine-L-lactic acid)/β-TCP composite material is obtained.

Figure 2:
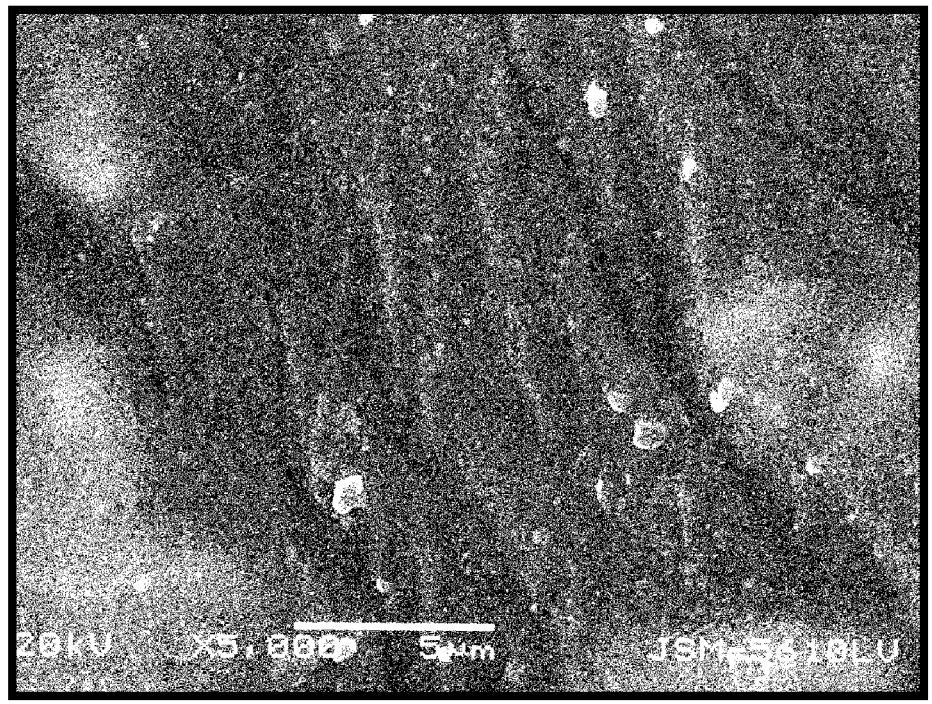
FIG. 2 is a schematic diagram of Microstructure of RGD polypeptide grafted poly (glycolic acid-L-lysine-L-lactic acid)/β-tricalcium phosphate composite material under the microscope (×5000).

As shown in the microstructure images (FIG. 1 and FIG. 2) of RGD polypeptide grafted poly (glycolic acid-L-lysine-L-lactic acid)/β-TCP composite material under 1000× and 5000× electron microscope, β-TCP particles are uniformly dispersed in the RGD polypeptide grafted poly (glycolic acid-L-lysine-L-lactic acid) matrix and the particle size of β-TCP particles is between 0.05 μm and 2 μm.

Embodiment 2

1) Preparing 3-[4-(Benzyloxycarbonylamino) Butyl]-Morpholine-2,5-Dione Monomer 50 ml triethylamine and 50 g $N^\epsilon$-benzyloxycarbonyl-L-Lysine are added to 500 ml 1,4-dioxane. Then 30 ml bromoacetyl bromide is dropped into the above-mentioned 1,4-dioxane solution at 5-10° C. The reaction is followed by TLC. The reaction product is extracted by diethyl ether twice. The extract is washed by water twice or three times, dried by sodium sulfate. The solvent is recovered in vacuum, and the residual products are used for next reaction.

The above-mentioned product is dropped to 1500 ml DMF suspension liquid containing 39 g $NaHCO_3$ at 50-110° C. The reaction is followed by TLC. After reclaiming of the solvent in vacuum, the reaction product is extracted by ethyl acetate several times, washed by water twice or three times and dried by sodium sulfate. After reclaiming of the solvent in vacuum, waxy solid is obtained. Then the waxy solid is dissolved in acetic ether and purified by column chromatography. After that, acetic ether is evaporated in vacuum and get the coarse product of 3-[4-(benzyloxycarbonylamino) butyl]-morpholine-2,5-dione monomer, which is finally recrystallized by acetic ether/n-hexane to obtain 3-[4-(benzyloxycarbonylamino) butyl]-morpholine-2,5-dione monomer.

2) Preparing Poly (Glycolic Acid-$N^\epsilon$-Benzyloxycarbonyl-L-Lysine-L-Lactic Acid)

According to the molar ratio of L-Lactide: 3-[4-(benzyloxycarbonylamino) butyl]-morpholine-2,5-dione monomer=1: 19, 42.75 g L-Lactide and 5 g 3-[4-(benzyloxycarbonylamino) butyl]-morpholine-2,5-dione monomer are weighed and put into ampule, and then inject 5 ml stannous octoate chloroform solution of 30 mg/ml. After volatilization of the chloroform under vacuum, the ampule is sealed with alcohol blast burner. Finally, the sealed ampule is put into oil-bath of 90-140° C. for 12-72 h to obtain poly (glycolic acid-$N^\epsilon$-benzyloxycarbonyl-L-lysine-L-lactic acid).

3) Preparing Poly (Glycolic Acid-L-Lysine-L-Lactic Acid)

20 g poly (glycolic acid-$N^\epsilon$-benzyloxycarbonyl-L-lysine-L-lactic acid) is dissolved in 200 ml chloroform and undergoes the catalytic hydrogenolysis by 1 g 10% Pd/C to eliminate benzyloxycarbonyl group, which results in poly (glycolic acid-L-lysine-L-lactic acid).

4) Preparing RGD Polypeptide Grafted Poly (Glycolic Acid-L-Lysine-L-Lactic Acid)

First, 10 g poly (glycolic acid-L-lysine-L-lactic acid) is dissolved in 300 ml $CH_2Cl_2$ and 450 ml DMSO is added. Then 0.2-0.6 g GRGDY short peptide and 0.3 g CDI are added to the above-mentioned solution. The mixture is kept for 3-5 h at 0-5° C. and then $CH_2Cl_2$ is reclaimed in vacuum. After residual liquid becoming opacity, water is added, and polymer is separated out. The polymer is filtered and dried in high vacuum to get the RGD polypeptide grafted poly (glycolic acid-L-lysine-L-lactic acid) with molecular weight of 50,000-250,000. The mole content of L-lysine in RGD polypeptide grafted poly (glycolic acid-L-lysine-L-lactic acid) is 1%-2.5%.

5) Synthesizing β-TCP Particle

β-TCP particles are synthesized by solid state method. When 34.4 g $CaHPO_4.2H_2O$ and 10 g $CaCO_3$ are mixed uniformly, the mixture is directly calcined at about 940° C. to obtain β-TCP powder. Then β-TCP powder is milled in water for 8-12 h by ball milling, and then dried. After that, the dried β-TCP powder is dispersed in absolute alcohol and classified. Then, the β-TCP powder is dried again to obtain β-TCP particles between 0.05 μm and 2 μm in diameter for standby.

6) Preparing an RGD Polypeptide Grafted Poly (Glycolic Acid-L-Lysine-L-Lactic Acid)/β-TCP Particle Composite Material First, 10 g RGD polypeptide grafted poly (glycolic acid-L-lysine-L-lactic acid) is dissolved in chloroform. Then 0.5 g β-TCP particles are added to the above-mentioned solution and dispersed by ultrasonic wave. After volatilization of solvent, RGD polypeptide grafted poly (glycolic acid-L-lysine-L-lactic acid)/β-TCP composite material is obtained.

Embodiment 3

1) Preparing 3-[4-(Benzyloxycarbonylamino) Butyl]-Morpholine-2,5-Dione Monomer 50 ml triethylamine and 50 g $N^\epsilon$-benzyloxycarbonyl-L-lysine are added to 500 ml 1,4-dioxane. Then drop 30 ml bromoacetyl bromide at 10-25° C. and follow the reaction by TLC. When the reaction is over, extract the product of reaction by diethyl ether twice. The extractions liquid is washed by water twice or three times, and sodium sulfate is added to dry. The solvent is reclaimed in vacuum, and the residual products are used for next reaction.

The above-mentioned product is dropped to 1500 ml DMF suspension liquid containing 39 g $NaHCO_3$ at 50-110° C. The reaction is followed by TLC. After reclaiming of the solvent in vacuum, the reaction product is extracted by ethyl acetate several times, washed by water twice or three times and dried by sodium sulfate. After reclaiming of the solvent in vacuum, waxy solid is obtained. Then the waxy solid is dissolved in acetic ether and purified by column chromatography. After that, acetic ether is evaporated in vacuum and obtain the coarse product of 3-[4-(benzyloxycarbonylamino) butyl]-morpholine-2,5-dione monomer, which is finally recrystallized by acetic ether/n-hexane to obtain 3-[4-(benzyloxycarbonylamino) butyl]-morpholine-2,5-dione monomer.

2) Preparing Poly (Glycolic Acid-$N^\epsilon$-Benzyloxycarbonyl-L-Lysine-L-Lactic Acid)

According to the molar ratio of L-Lactide: 3-[4-(benzyloxycarbonylamino) butyl]-morpholine-2,5-dione monomer=1: 49, 44.2 g L-Lactide and 2 g 3-[4-(benzyloxycarbonylamino) butyl]-morpholine-2,5-dione monomer are weighed and put into ampule. Then 5 ml stannous octoate chloroform solution of 30 mg/ml is injected. After volatilization of the chloroform under vacuum, the ampule is sealed with alcohol blast burner. Finally, the sealed ampule is put into oil-bath of 90-140° C. for 12-72 h to obtain poly (glycolic acid-$N^\epsilon$-benzyloxycarbonyl-L-lysine-L-lactic acid).

3) Preparing Poly (Glycolic Acid-L-Lysine-L-Lactic Acid)

20 g poly (glycolic acid-$N^\epsilon$-benzyloxycarbonyl-L-lysine-L-lactic acid) is dissolved in 200 ml chloroform and undergoes the catalytic hydrogenolysis by 1 g 10% Pd/C to eliminate benzyloxycarbonyl group, which results in poly (glycolic acid-L-lysine-L-lactic acid).

4) Preparing RGD Polypeptide Grafted Poly (Glycolic Acid-L-Lysine-L-Lactic Acid)

First, dissolve 10 g poly (glycolic acid-L-lysine-L-lactic acid) in 300 ml $CH_2Cl_2$ and add 450 ml DMSO. Then 0.03-0.3 g GRGDY short peptide and 0.1 g CDI are added to the above-mentioned solution. The mixture is kept for 3-5 h at 0-5° C. and then $CH_2Cl_2$ is reclaimed in vacuum. After residual liquid becoming opacity, water is added, and polymer is separated out. The polymer is filtered and dried in high vacuum to obtain the RGD polypeptide grafted poly (glycolic acid-L-lysine-L-lactic acid) with molecular weight of 80,000-300,000. The mole content of L-lysine in RGD polypeptide grafted poly (glycolic acid-L-lysine-L-lactic acid) is 0.1%-1%.

5) Synthesizing β-TCP Particle

β-TCP particles are synthesized by solid state method. After 34.4 g $CaHPO_4.2H_2O$ and 10 g $CaCO_3$ are mixed uniformly, the mixture is directly calcined at about 940° C. to obtain β-TCP powder. Then β-TCP powder is milled in water for 8-12 h by ball milling, and then dried. After that, the dried β-TCP powder is dispersed in absolute alcohol and classified. Then, the β-TCP powder is dried again to obtain β-TCP particles between 0.05 μm and 2 μm in diameter for standby.

6) Preparing an RGD Polypeptide Grafted Poly (Glycolic Acid-L-Lysine-L-Lactic Acid)/β-TCP Particle Composite Material First, 10 g RGD polypeptide grafted poly (glycolic acid-L-lysine-L-lactic acid) is dissolved in chloroform. Then 1 g β-TCP particles are added to the above-mentioned solution and dispersed by ultrasonic wave. After volatilization of solvent, RGD polypeptide grafted poly (glycolic acid-L-lysine-L-lactic acid)/β-TCP composite material is obtained.

What is claimed is:

1. An RGD polypeptide grafted poly (glycolic acid-L-lysine-L-lactic acid)/β-tricalcium phosphate composite material, comprising a two-phase mixture of β-tricalcium phosphate particles and RGD polypeptide grafted poly (glycolic acid-L-lysine-L-lactic acid), the RGD polypeptide grafted poly (glycolic acid-L-lysine-L-lactic acid) consisting of the following molecular structure:

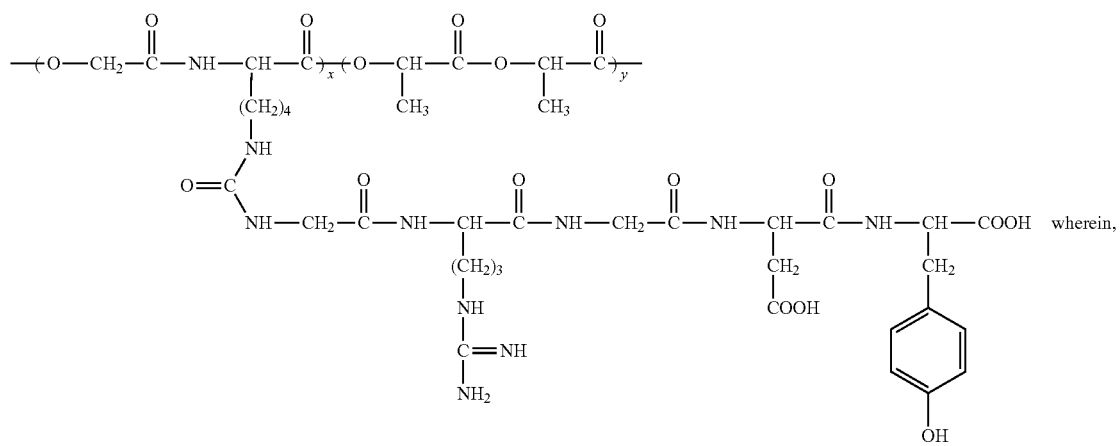

wherein,
the number average molecular weight of RGD polypeptide grafted poly (glycolic acid-L-lysine-L-lactic acid) is 30,000-300,000;
the mole content of L-lysine in RGD polypeptide grafted poly (glycolic acid-L-lysine-L-lactic acid) is 0.1%-5%;
β-tricalcium phosphate particles are uniformly dispersed in the RGD polypeptide grafted poly (glycolic acid-L-lysine-L-lactic acid) matrix, and
the mass ratio of β-tricalcium phosphate particles and RGD polypeptide grafted poly (glycolic acid-L-lysine-L-lactic acid) is between 1:10 and 1:100.

2. The RGD polypeptide grafted poly (glycolic acid-L-lysine-L-lactic acid)/β-tricalcium phosphate composite material according to claim 1, wherein said particle size of β-tricalcium phosphate particles is between 0.05 μm and 2 μm.

3. The material of claim 2, wherein the mass ratio of β-tricalcium phosphate particles and RGD polypeptide grafted poly (glycolic acid-L-lysine-L-lactic acid) is between 1:10 and 1:50.

4. The RGD polypeptide grafted poly (glycolic acid-L-lysine-L-lactic acid)/β-tricalcium phosphate composite material according to claim 1, wherein the mass ratio of β-tricalcium phosphate particles and RGD polypeptide grafted poly (glycolic acid-L-lysine-L-lactic acid) is between 1:10 and 1:50.

5. The polypeptide grafted poly (glycolic acid-L-lysine-L-lactic acid)/β-tricalcium phosphate composite material of claim 1, wherein the particle size of β-tricalcium phosphate particles is from 0.05 μm up to but not including 1 μm.

6. The polypeptide grafted poly (glycolic acid-L-lysine-L-lactic acid)/β-tricalcium phosphate composite material of claim 1, wherein the particle size of β-tricalcium phosphate particles is less than 1 μm.

7. The polypeptide grafted poly (glycolic acid-L-lysine-L-lactic acid)/β-tricalcium phosphate composite material of claim 1, wherein the number average molecular weight of RGD polypeptide grafted poly (glycolic acid-L-lysine-L-lactic acid) is 50,000-250,000.

8. The polypeptide grafted poly (glycolic acid-L-lysine-L-lactic acid)/β-tricalcium phosphate composite material of claim 1, wherein the number average molecular weight of RGD polypeptide grafted poly (glycolic acid-L-lysine-L-lactic acid) is 80,000-300,000.

9. The polypeptide grafted poly (glycolic acid-L-lysine-L-lactic acid)/β-tricalcium phosphate composite material of claim 1, wherein the polypeptide grafted poly (glycolic acid-L-lysine-L-lactic acid)/β-tricalcium phosphate composite material is provided in the form of a nerve guide for repairing nerve tissue.

10. The polypeptide grafted poly (glycolic acid-L-lysine-L-lactic acid)/β-tricalcium phosphate composite material of claim 1, wherein the polypeptide grafted poly (glycolic acid-L-lysine-L-lactic acid)/β-tricalcium phosphate composite material is provided in the form of a porous bone scaffold for repairing bone tissue.

11. An RGD polypeptide grafted poly (glycolic acid-L-lysine-L-lactic acid)/β-tricalcium phosphate composite material, comprising a two-phase mixture of: (i) β-tricalcium phosphate particles, and (ii) RGD polypeptide grafted poly (glycolic acid-L-lysine-L-lactic acid), the RGD polypeptide grafted poly (glycolic acid-L-lysine-L-lactic acid) consisting of the following molecular structure:

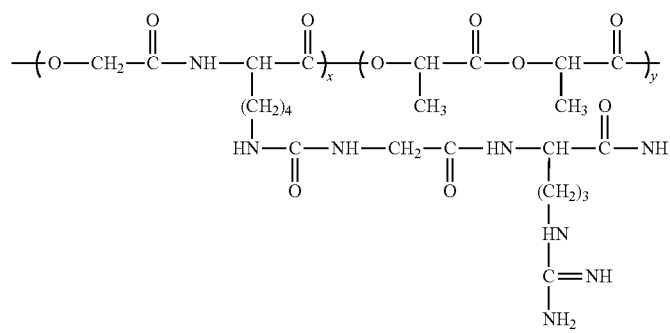

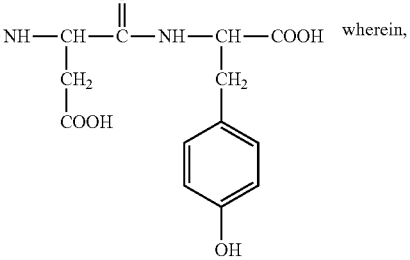 wherein, the mole content of L-lysine in RGD polypeptide grafted poly (glycolic acid-L-lysine-L-lactic acid) is 0.1%-5%;
β-tricalcium phosphate particles are uniformly dispersed in the RGD polypeptide grafted poly (glycolic acid-L-lysine-L-lactic acid) matrix, and
the mass ratio of β-tricalcium phosphate particles and RGD polypeptide grafted poly (glycolic acid-L-lysine-L-lactic acid) is between 1:10 and 1:100.

12. The polypeptide grafted poly (glycolic acid-L-lysine-L-lactic acid)/β-tricalcium phosphate composite material of claim 11, wherein the particle size of β-tricalcium phosphate particles is from 0.05 μm up to but not including 1 μm.

13. An RGD polypeptide grafted poly (glycolic acid-L-lysine-L-lactic acid)/β-tricalcium phosphate composite material, comprising a two-phase mixture of: (i) β-tricalcium phosphate particles, and (ii) RGD polypeptide grafted poly (glycolic acid-L-lysine-L-lactic acid), the RGD polypeptide grafted poly (glycolic acid-L-lysine-L-lactic acid) consisting of the following molecular structure:

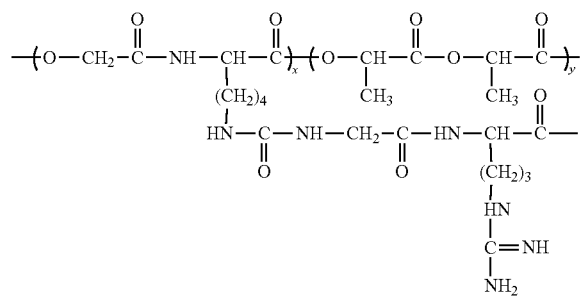

-continued

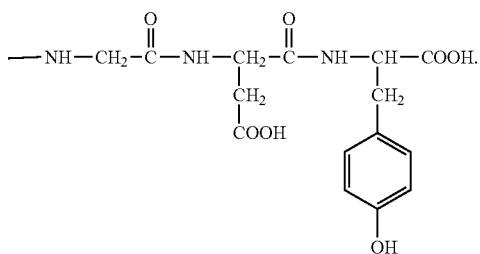

14. The RGD polypeptide grafted poly (glycolic acid-L-lysine-L-lactic acid)/β-tricalcium phosphate composite material of claim 13, wherein X:Y is between 1:10 and 1:100.

15. The polypeptide grafted poly (glycolic acid-L-lysine-L-lactic acid)/β-tricalcium phosphate composite material of claim 13, wherein the particle size of β-tricalcium phosphate particles is from 0.05 μm up to but not including 1 μm.

* * * * *